(12) United States Patent
Niazi et al.

(10) Patent No.: US 12,247,086 B2
(45) Date of Patent: Mar. 11, 2025

(54) ENHANCED IMMUNOGENICITY FOR GPI-ANCHORED ANTIGENS

(71) Applicant: NantBio, Inc., Culver City, CA (US)

(72) Inventors: Kayvan Niazi, Culver City, CA (US); Wael Tadros, Culver City, CA (US); Annie Shin, Culver City, CA (US)

(73) Assignee: NantBio, Inc., Culver City, CA (US)

( * ) Notice: Subject to any disclaimer, the term of this patent is extended or adjusted under 35 U.S.C. 154(b) by 0 days.

(21) Appl. No.: 18/339,155

(22) Filed: Jun. 21, 2023

(65) Prior Publication Data

US 2024/0018274 A1      Jan. 18, 2024

Related U.S. Application Data

(62) Division of application No. 16/959,424, filed as application No. PCT/US2019/013633 on Jan. 15, 2019, now Pat. No. 11,773,187.

(60) Provisional application No. 62/618,087, filed on Jan. 17, 2018.

(51) Int. Cl.
| | | |
|---|---|---|
| *C07K 14/47* | (2006.01) | |
| *A61K 39/00* | (2006.01) | |
| *C07K 14/575* | (2006.01) | |
| *C07K 14/725* | (2006.01) | |
| *C07K 19/00* | (2006.01) | |
| *C12N 5/078* | (2010.01) | |
| *C12N 15/10* | (2006.01) | |
| *C12N 15/86* | (2006.01) | |

(52) U.S. Cl.
CPC .............. *C07K 19/00* (2013.01); *A61K 39/00* (2013.01); *A61K 39/001182* (2018.08); *A61K 39/461* (2023.05); *A61K 39/4622* (2023.05); *A61K 39/464482* (2023.05); *C07K 14/575* (2013.01); *C07K 14/7051* (2013.01); *C12N 15/102* (2013.01); *C12N 15/86* (2013.01); *C07K 2319/912* (2013.01); *C12N 2710/10111* (2013.01)

(58) Field of Classification Search
CPC .. C07K 19/00; C07K 14/575; C07K 14/7051; C07K 2319/912; C12N 15/102; C12N 15/86; C12N 2710/10111

See application file for complete search history.

(56) References Cited

U.S. PATENT DOCUMENTS

| | | |
|---|---|---|
| 7,758,891 B2 | 7/2010 | Desai et al. |
| 7,771,751 B2 | 8/2010 | Desai et al. |
| 7,780,984 B2 | 8/2010 | Desai et al. |
| 7,981,445 B2 | 7/2011 | De et al. |
| 8,034,375 B2 | 10/2011 | Desai et al. |
| 10,285,955 B2 | 5/2019 | Kelner |
| 2005/0281816 A1 | 12/2005 | Amping et al. |
| 2008/0311137 A1 | 12/2008 | Monica et al. |
| 2014/0134201 A1 | 5/2014 | Tureci et al. |

FOREIGN PATENT DOCUMENTS

| | | |
|---|---|---|
| CN | 105007941 A | 10/2015 |
| CN | 107573419 A | 1/2018 |
| WO | 03/066820 A2 | 8/2003 |
| WO | 2005/071088 A2 | 8/2005 |
| WO | 2011/139345 A3 | 3/2012 |
| WO | 2013/062505 A1 | 5/2013 |
| WO | 2016/172722 A1 | 10/2016 |
| WO | 2019/143606 A1 | 7/2019 |

OTHER PUBLICATIONS

Andrea Pierleoni et al., "PredGPI: a GPI-anchor predictor" BMC Bioinformatics 2008, 9:392 doi:10.1186/1471-2105-9-392.
Angela Barth et al., "Replacement of the Phospholipid-Anchor in the Contact Site A Glycoprotein of D. discoideum by a Transmembrane Region Does Not Impede Cell Adhesion but Reduces Residence Time on the Cell Surface" The Journal of Cell Biology, vol. 124, 1994 pp. 1-11.
Carmen Galian et al., "Efficient Glycosylphosphatidylinositol (GPI) Modification of Membrane Proteins Requires a C-terminal Anchoring Signal of Marginal Hydrophobicity" The Journal of Biological Chemistry vol. 287, No. 20, pp. 16399-16409, May 11, 2012.
David R. Taylor and Nigel M. Hooper "GPI-Anchored Proteins in Health and Disease" Chapter 2, C.J. Vidal (ed.), Post-Translational Modifications in Health and Disease, 2011, pp. 39-55.
International Search Report, International Filing No. PCT/US2019/013633 dated: Jan. 15, 2019, pp. 1-13.
John P. Incardona and Terrone L. Rosenberry "Replacement of the Glycoinositol Phospholipid Anchor of Drosophila Acetylcholinesterase with a Transmembrane Domain Does Not Alter Sorting in Neurons and Epithelia but Results in Behavioral Defects" Molecular Biology of the Cell vol. 7, 613-630, Apr. 1996.
Kailash N. Pandey "Functional roles of short sequence motifs in the endocytosis of membrane receptors" Front Biosci (Landmark Ed).; 14: 5339-5360.
Margot G. Paulick‡ and Carolyn R. Bertozzi "The Glycosylphosphatidylinositol Anchor: A Complex Membrane-Anchoring Structure for Proteins" Biochemistry 2008, 47, 6991-7000.
Michael J. Duffy, "Carcinoembryonic Antigen as a Marker for Colorectal Cancer: Is It Clinically Useful?" Clinical Chemistry 47:4 624-630 (2001).
Naama Hurwitz et al., "Towards genome-scale structure prediction for transmembrane proteins" Phil. Trans. R. Soc. B (2006) 361, 465-475.

(Continued)

*Primary Examiner* — Julie Ha
*Assistant Examiner* — Kristina M Hellman
(74) *Attorney, Agent, or Firm* — Martin Fessenmaier; Umberg Zipser LLP

(57) ABSTRACT

Compositions and methods are presented that allow for an enhanced immune response against a GPI-anchored tumor associated antigen by modification of the protein portion of the TAA to include a transmembrane domain and a trafficking signal that directs the modified protein to the endosomal or lysosomal compartment. Most preferably, the modified protein will no longer have a GPI anchor or GPI attachment sequence.

18 Claims, 6 Drawing Sheets

Specification includes a Sequence Listing.

(56) References Cited

OTHER PUBLICATIONS

Niklaus Fankhauser and Pascal Maser, "Identification of GPI anchor attachment signals by a Kohonen self-organizing map" Bioinformatics vol. 21 No. 9 2005, pp. 1846-1852.
Peng Zhao et al., "Proteomic Identification of Glycosylphosphatidylinositol Anchor-dependent Membrane Proteins Elevated in Breast Carcinoma" The Journal of Biological Chemistry vol. 287, No. 30, pp. 25230-25240, Jul. 20, 2012.
Predrag Radivojac et al., "Identification, Analysis and Prediction of Protein Ubiquitination Sites" Proteins. Feb. 1, 2010; 78(2): 365-380. doi:10.1002/prot.22555.
Xiaoying Chen et al., "Fusion Protein Linkers: Property, Design and Functionality" Adv Drug Deliv Rev. Oct. 1, 20135; 65(10): 1357-1369. doi:10.1016/j.addr.2012.09.039.
Jones et al., "A Model Recognition Approach to the Prediction of All-Helical Membrane Protein Structure and Topology", Biochemistry, 1994, vol. 33, pp. 3038-3049.
Vijayasaradhi et al., "Intracellular Sorting and Targeting of Melanosomal Membrane Proteins: Identification of Signals for Sorting of the Human Brown Locus Protein, GP75", The Journal of Cell Biology, 1995, vol. 130, pp. 807-820.
Mahnke et al., "The Dendritic Cell Receptor for Endocytosis, DEC-205, Can Recycle and Enhance Antigen Presentation via Major Histocompatibility Complex Class II-positive Lysosomal Compartments", The Journal of Cell Biology, 2000, vol. 151, No. 3, pp. 673-683.
Bonifacino et al., "Signals for Sorting of Transmembrane Proteins to Endosomes and Lysosomes", Annual Review of Biochemistry, 2003, vol. 72, pp. 395-447.
International Preliminary Report on Patentability Chapter I received for PCT Application Serial No. PCT/US2019/013633 dated Jul. 30, 2020, 8 pages.
Extended European Search Report received for European Patent Application Serial No. 19741284.4 dated Sep. 16, 2021, 6 pages.
First Office Action received for Chinese Patent Application Serial No. 201980009104.X dated Jul. 6, 2023, 20 pages. (Including English Translation).
Restriction Requirement received for U.S. Appl. No. 16/959,424 dated Jun. 14, 2022, 11 pages.
Non-Final Office Action received for U.S. Appl. No. 16/959,424 dated Sep. 2, 2022, 50 pages.
Notice of Allowance received for U.S. Appl. No. 16/959,424 dated Jun. 16, 2023, 25 pages.

```
                       SEQUENCE LISTING

Sequence total quantity: 5
SEQ ID NO: 1           moltype = AA  length = 702
FEATURE                Location/Qualifiers
REGION                 1..702
                       note = Synthesized in Laboratory CEA1
source                 1..702
                       mol_type = protein
                       organism = synthetic construct
SEQUENCE: 1
MESPSAPPHR WCIPWQRLLL TASLLTFWNP PTTAKLTIES TPFNVAEGKE VLLLVHNLPQ  60
HLFGYSWYKG ERVDGNRQII GYVIGTQQAT PGPAYSGREI IYPNASLLIQ NIIQNDTGFY 120
TLHVIKSDLV NEEATGQFRV YPELPKPSIS SNNSKPVEDK DAVAFTCEPE TQDATYLWWV 180
NNQSLPVSPR LQLSNGNRTL TLFNVTRNDT ASYKCETQNP VSARRSDSVI LNVLYGPDAP 240
TISPLNTSYR SGENLNLSCH AASNPPAQYS WFVNGTFQQS TQELFIPNIT VNNSGSYTCQ 300
AHNSDTGLNR TTVTTITVYA EPPKPFITSN NSNPVEDEDA VALTCEPEIQ NTTYLWWVNN 360
QSLPVSPRLQ LSNDNRTLTL LSVTRNDVGP YECGIQNELS VDHSDPVILN VLYGPDDPTI 420
SPSYTYYRPG VNLSLSCHAA SNPPAQYSWL IDGNIQQHTQ ELFISNITEK NSGLYTCQAN 480
NSASGHSRTT VKTITVSAEL PKPSISSNNS KPVEDKDAVA FTCEPEAQNT TYLWWVNGQS 540
LPVSPRLQLS NGNRTLTLFN VTRNDARAYV CGIQNSVSAN RSDPVTLDVL YGPDTPIISP 600
PDSSYLSGAD LNLSCHSASN PSPQYSWRIN GIPQQHTQVL FIAKITPNNN GTYACFVSNL 660
ATGRNNSIVK SITVSASGTS PGLSAGATVG IMIGVLVGVA LI                  702

SEQ ID NO: 2           moltype = AA  length = 705
FEATURE                Location/Qualifiers
REGION                 1..705
                       note = Synthesized in Laboratory CEA1-CD1a
source                 1..705
                       mol_type = protein
                       organism = synthetic construct
SEQUENCE: 2
MESPSAPPHR WCIPWQRLLL TASLLTFWNP PTTAKLTIES TPFNVAEGKE VLLLVHNLPQ  60
HLFGYSWYKG ERVDGNRQII GYVIGTQQAT PGPAYSGREI IYPNASLLIQ NIIQNDTGFY 120
TLHVIKSDLV NEEATGQFRV YPELPKPSIS SNNSKPVEDK DAVAFTCEPE TQDATYLWWV 180
NNQSLPVSPR LQLSNGNRTL TLFNVTRNDT ASYKCETQNP VSARRSDSVI LNVLYGPDAP 240
TISPLNTSYR SGENLNLSCH AASNPPAQYS WFVNGTFQQS TQELFIPNIT VNNSGSYTCQ 300
AHNSDTGLNR TTVTTITVYA EPPKPFITSN NSNPVEDEDA VALTCEPEIQ NTTYLWWVNN 360
QSLPVSPRLQ LSNDNRTLTL LSVTRNDVGP YECGIQNELS VDHSDPVILN VLYGPDDPTI 420
SPSYTYYRPG VNLSLSCHAA SNPPAQYSWL IDGNIQQHTQ ELFISNITEK NSGLYTCQAN 480
NSASGHSRTT VKTITVSAEL PKPSISSNNS KPVEDKDAVA FTCEPEAQNT TYLWWVNGQS 540
LPVSPRLQLS NGNRTLTLFN VTRNDARAYV CGIQNSVSAN RSDPVTLDVL YGPDTPIISP 600
PDSSYLSGAD LNLSCHSASN PSPQYSWRIN GIPQQHTQVL FIAKITPNNN GTYACFVSNL 660
ATGRNNSIVK SITVMLIPIA VGGALAGLVL IVLIAYLIGR KRCFC               705

SEQ ID NO: 3           moltype = AA  length = 709
FEATURE                Location/Qualifiers
REGION                 1..709
                       note = Synthesized in Laboratory CEA1-CD1c
source                 1..709
                       mol_type = protein
                       organism = synthetic construct
SEQUENCE: 3
MESPSAPPHR WCIPWQRLLL TASLLTFWNP PTTAKLTIES TPFNVAEGKE VLLLVHNLPQ  60
HLFGYSWYKG ERVDGNRQII GYVIGTQQAT PGPAYSGREI IYPNASLLIQ NIIQNDTGFY 120
TLHVIKSDLV NEEATGQFRV YPELPKPSIS SNNSKPVEDK DAVAFTCEPE TQDATYLWWV 180
NNQSLPVSPR LQLSNGNRTL TLFNVTRNDT ASYKCETQNP VSARRSDSVI LNVLYGPDAP 240
TISPLNTSYR SGENLNLSCH AASNPPAQYS WFVNGTFQQS TQELFIPNIT VNNSGSYTCQ 300
AHNSDTGLNR TTVTTITVYA EPPKPFITSN NSNPVEDEDA VALTCEPEIQ NTTYLWWVNN 360
QSLPVSPRLQ LSNDNRTLTL LSVTRNDVGP YECGIQNELS VDHSDPVILN VLYGPDDPTI 420
```

```
SPSYTYYRPG VNLSLSCHAA SNPPAQYSWL IDGNIQQHTQ ELFISNITEK NSGLYTCQAN  480
NSASGHSRTT VKTITVSAEL PKPSISSNNS KPVEDKDAVA FTCEPEAQNT TYLWWVNGQS  540
LPVSPRLQLS NGNRTLTLFN VTRNDARAYV CGIQNSVSAN RSDPVTLDVL YGPDTPIISP  600
PDSSYLSGAD LNLSCHSASN PSPQYSWRIN GIPQQHTQVL FIAKITPNNN GTYACFVSNL  660
ATGRNNSIVK SITVMLIPIA VGGALAGLVL IVLIAYLIGK KHCSYQDIL              709

SEQ ID NO: 4            moltype = AA  length = 710
FEATURE                 Location/Qualifiers
REGION                  1..710
                        note = Synthesized in Laboratory CEA1-LAMP1
source                  1..710
                        mol_type = protein
                        organism = synthetic construct
SEQUENCE: 4
MESPSAPPHR WCIPWQRLLL TASLLTFWNP PTTAKLTIES TPFNVAEGKE VLLLVHNLPQ  60
HLFGYSWYKG ERVDGNRQII GYVIGTQQAT PGPAYSGREI IYPNASLLIQ NIIQNDTGFY  120
TLHVIKSDLV NEEATGQFRV YPELPKPSIS SNNSKPVEDK DAVAFTCEPE TQDATYLWWV  180
NNQSLPVSPR LQLSNGNRTL TLFNVTRNDT ASYKCETQNP VSARRSDSVI LNVLYGPDAP  240
TISPLNTSYR SGENLNLSCH AASNPPAQYS WFVNGTFQQS TQELFIPNIT VNNSGSYTCQ  300
AHNSDTGLNR TTVTTITVYA EPPKPFITSN NSNPVEDEDA VALTCEPEIQ NTTYLWWVNN  360
QSLPVSPRLQ LSNDNRTLTL LSVTRNDVGP YECGIQNELS VDHSDPVILN VLYGPDDPTI  420
SPSYTYYRPG VNLSLSCHAA SNPPAQYSWL IDGNIQQHTQ ELFISNITEK NSGLYTCQAN  480
NSASGHSRTT VKTITVSAEL PKPSISSNNS KPVEDKDAVA FTCEPEAQNT TYLWWVNGQS  540
LPVSPRLQLS NGNRTLTLFN VTRNDARAYV CGIQNSVSAN RSDPVTLDVL YGPDTPIISP  600
PDSSYLSGAD LNLSCHSASN PSPQYSWRIN GIPQQHTQVL FIAKITPNNN GTYACFVSNL  660
ATGRNNSIVK SITVMLIPIA VGGALAGLVL IVLIAYLIGR KRSHAGYQTI             710

SEQ ID NO: 5            moltype = AA  length = 25
FEATURE                 Location/Qualifiers
REGION                  1..25
                        note = Transmembrane domain
source                  1..25
                        mol_type = protein
                        organism = synthetic construct
SEQUENCE: 5
MLIPIAVGGA LAGLVLIVLI AYLIG                                       25
```

ENHANCED IMMUNOGENICITY FOR GPI-ANCHORED ANTIGENS

This application is a divisional of pending U.S. patent application Ser. No. 16/959,424, filed on Jun. 30, 2020, which claims priority to our US provisional application with the Ser. No. 62/618,087, which was filed Jan. 17, 2018.

SEQUENCE LISTING

The content of the ASCII text file of the sequence listing named 102719.0010US2.XML, which is 10,096 bytes in size was created on Jun. 21, 2023 and electronically submitted via EFS-Web, and is incorporated by reference in its entirety.

FIELD OF THE INVENTION

The field of the invention is compositions and methods of enhanced immunogenicity for antigens, especially as it relates to various compositions and methods that enhance the immunogenicity of GPI-anchored antigens in cancer therapy.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Significant improvements have been made in cancer immunotherapies targeting patient- and tumor specific antigens (neoepitopes). While promising, identification of suitable antigens and subsequent creation of tailored therapeutic compositions is time consuming and expensive. Alternatively, immune therapy can also target antigens that are common to specific tumors (i.e., tumor associated antigens (TAA)). However, not all TAAs are equally effective across a diverse group of patients, and several TAAs tend to be entirely ineffective as an immunogenic entity due to glycophosphatidylinositol (GPI) anchoring to the cell membrane, and FIG. 1 schematically illustrates the structure of a GPI anchor.

Unfortunately, various TAAs are GPI-anchored proteins and especially include CEA (carcinoembryonic antigen, often associated with epithelial cancers), PSCA (prostate stem cell antigen), mesothelin (often associated with mesothelioma, ovarian and pancreatic adenocarcinoma), and urokinase plasminogen activator receptor (often associated with aggressive cancer growth and metastasis in many cancers, for example, gastric cancer) and as such will typically not be effective targets for cancer immune therapy.

While membrane anchors could conceptually be removed from a protein, thusly modified proteins will in most circumstances not be translocated to the cell surface and so fail to exert proper function. On the other hand, certain phospholipid anchors of a membrane anchored glycoprotein can be replaced with a transmembrane domain as was shown for slime mold *Dictyostelium discoideum*. However, such replacement substantially reduced residence time on the cell surface (*Cell Biol.*, Volume 124, Numbers 1 & 2, January 1994 205-215), and so modified proteins are therefore less likely to be bound by an antibody.

Thus, even though various TAAs may conceptually serve as therapeutic targets common to many cancers and as such may eliminate the need for personalized therapy, not all of the TAA are sufficiently immunogenic. Consequently, there is a need to provide improved compositions and methods that enhance immunogenicity of TAA, and especially GPI-anchored TAA.

SUMMARY OF THE INVENTION

The inventive subject matter is directed to various immune therapeutic compositions and methods in which GPI-anchored antigens are modified such that the modified antigen will no longer be coupled to a GPI portion but instead include one or more transmembrane domains and a cytoplasmic tail sequence derived or adapted from a protein that traffics the antigen to the endosomal or lysosomal system (e.g. CD1a, CD1c, Lamp1 portion). Such modified antigens resulted in increased CD4+ stimulation (relative to unmodified GPI-anchored antigen) and also resulted in increased stimulation of (polyfunctional) CD8+ T cells.

In one aspect of the inventive subject matter, the inventor contemplates a recombinant hybrid protein that comprises an antigen portion that is coupled to at least one transmembrane domain and a trafficking element. In preferred aspects, the antigen portion is at least a portion of a GPI-anchored protein, and the trafficking element directs the recombinant hybrid protein to a sub-cellular location (typically recycling endosome, sorting endosome, or lysosome).

For example, suitable GPI-anchored proteins are TAAs and especially include CEA, PSCA, mesothelin, and the urokinase plasminogen activator receptor, as well as non-cancer disease associated protein (e.g., variant surface protein of *Trypanosoma brucei* or a prion protein). In other examples, the antigen portion lacks a functional GPI anchoring signal, and/or the transmembrane domain comprises at least a portion of a transmembrane domain of an alpha, beta, or zeta chain of a T-cell receptor, CD28, CD3 epsilon, CD45, CD4, CD5, CD8 (e.g., CD8 alpha, CD8 beta), CD9, CD16, CD22, CD33, CD37, CD64, CD80, CD86, CD134, CD137, CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, or PAG/Cbp.

While not limiting to the inventive subject matter, the transmembrane domain is preferably bound in-frame to the C-terminus of the antigen portion (with or without a peptide linker), and most preferably includes an endosomal trafficking element of CD1a, CD1c, or Lamp 1. Furthermore, it is generally preferred that the trafficking element is bound in-frame to the C-terminus of the transmembrane domain.

In a further contemplated aspect of the inventive subject matter, the inventor also contemplates a recombinant nucleic acid that comprises a sequence segment encoding the hybrid protein as contemplated herein, operably linked to a promoter to drive expression of the hybrid protein. Most typically, the recombinant nucleic acid is a viral expression vector (e.g., an adenoviral expression vector, preferably having a deleted E1 and E2b gene), and the promoter is a constitutive promoter or an inducible promoter (e.g., inducible by hypoxia, IFN-gamma, or IL-8). In addition, contemplated recombinant nucleic acids may further comprise a sequence that encodes at least one of a co-stimulatory molecule, an immune stimulatory cytokine, a protein that interferes with or down-regulates checkpoint inhibition, and an adjuvant polypeptide.

Suitable co-stimulatory molecules include OX40L, 4-1BBL, CD80, CD86, CD30, CD40, CD30L, CD40L, ICOS-L, B7-H3, B7-H4, CD70, GITR-L, TIM-3, TIM-4, CD48, CD58, TL1A, ICAM-1, and LFA3, while contemplated immune stimulatory cytokines include IL-2, IL-12, IL-15, IL-15 super agonist (ALT803), IL-21, IPS1, and LMP1, and suitable proteins that interfere include an antibody or an antagonist of CTLA-4, PD-1, TIM1 receptor, 2B4, or CD160. Contemplated adjuvant polypeptides include calreticulin or a portion with adjuvant activity thereof, or HMGB1 or a portion with adjuvant activity thereof.

Viewed from a different perspective, the inventor also contemplates recombinant virus comprising the recombinant nucleic acid presented herein, and especially a replication deficient virus (e.g., adenovirus having a deleted E1 and E2b gene). Likewise, recombinant antigen presenting cell are also contemplated that comprise the recombinant nucleic acids presented herein.

In yet another aspect of the inventive subject matter, the inventor also contemplates a method of increasing antigenicity of a GPI-anchored protein that includes a step of modifying the protein portion of the GPI-anchored protein to include at least one transmembrane domain and a trafficking element, wherein the trafficking element directs the modified protein to a sub-cellular location (e.g., recycling endosome, sorting endosome, or lysosome). With respect to the GPI-anchored protein it is preferred that the protein is a TAA (such as CEA, PSCA, mesothelin, or urokinase plasminogen activator receptor) or that the protein is a non-cancer disease associated protein, optionally a variant surface protein of *Trypanosoma brucei* or a prion protein.

Therefore, the inventor also contemplates a method of treating a tumor expressing a GPI-anchored tumor associated antigen that includes a step of administering a cell-based vaccine composition comprising contemplated recombinant hybrid proteins, or a step of administering a DNA or RNA-based vaccine composition that comprises contemplated recombinant nucleic acids.

For example, suitable cell-based vaccine compositions may comprise a plurality of recombinant autologous cells of the patient (preferably antigen presenting cells), or may comprise recombinant yeast or bacterial cells. Similarly, the DNA or RNA-based vaccine composition may comprise a recombinant adenovirus. Thus, contemplated pharmaceutical compositions may include a recombinant virus or a recombinant antigen presenting cell as presented herein (typically formulated for transfusion). Viewed from a different perspective, the inventor also contemplates the use of a recombinant virus as presented herein in the treatment of cancer, and the use of a recombinant nucleic acid as presented herein in the manufacture of a vaccine composition for treatment of cancer.

Various objects, features, aspects and advantages of the inventive subject matter will become more apparent from the following detailed description of preferred embodiments, along with the accompanying drawing in which like numerals represent like components.

DETAILED DESCRIPTION

Figure 1:
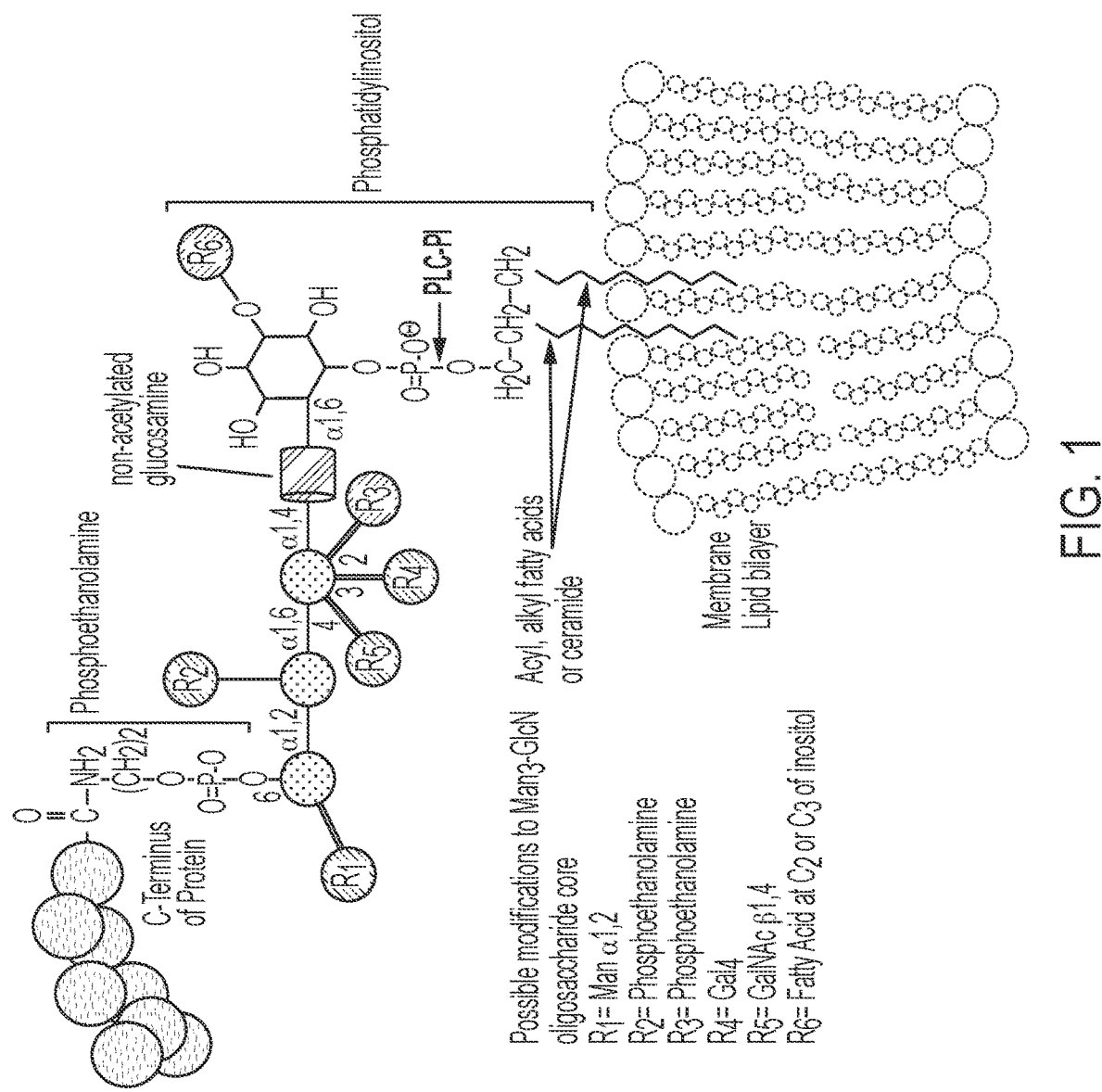
FIG. 1 is a schematic illustration of an exemplary GPI-anchored protein.

The inventor has now discovered that GPI-anchored membrane proteins, and especially disease associated GPI-anchored membrane proteins, can be genetically modified to so enhance their immunogenicity and render such antigens suitable targets for immune therapy. Notably, by modification of the proteins to drive them into the WIC II pathway, robust CD4+ cell activation can be achieved, enabling cross-presentation, and support of CD8+ cell growth via CD4 "helper" function. Such approach is especially advantageous where the GPI-anchored membrane protein is a TAA such as CEA, which is heavily prevalent on epithelial cancers. Due to the GPI anchor, CEA is generally not a therapeutically effective antigen for stimulating CD8 T cells in its natural configuration. However, modification of GPI-anchored membrane proteins as presented herein substantially increases immunogenicity and may thus render GPI-anchored membrane proteins therapeutic targets.

For example, and as discussed in more detail below, by replacing the GPI anchor on CEA with a transmembrane domain and cytoplasmic tail sequences derived from proteins which enter the endosomal system (e.g., CD1a, CD1c, Lamp1), the inventor demonstrated that such modified proteins achieve increased CD4 T cell responses (e.g., assessed as a frequency of antigen specific IFN gamma secreting cells and as a frequency of TNF-α/IFN-γ secreting polyfunctional T cells, which are the desired immunological subtype for fighting cancer). Most notably, targeting CEA to the endosomal system using the modifications presented herein also stimulated both the numbers of IFN-γ secreting CD8 T cells as well as the polyfunctional variety of these cells. As will be readily appreciated, such findings are relevant to other TAA such as mesothelin, PSCA, and urokinase plasminogen activator receptor, GPI-anchored proteins encoded by pathogens, or even GPI-anchored proteins against which an immunosuppressive response is desired like in autoimmunity through the inclusion of immune inhibitory factors (like IL-10, TGF-β, etc.). Further suitable GPI-anchored proteins and attachment signals can be readily identified using bioinformatics analysis (see e.g., *Bioinformatics* 2005, Vol. 21 no. 9 2005, pages 1846-1852; *BMC Bioinformatics* 2008, 9:392), while known GPI-anchored proteins can be retrieved from various publically accessible databases (e.g., URL: uniprot.org).

Therefore, the inventors generally contemplate genetic modifications of GPI-anchored proteins, and especially disease associated GPI-anchored proteins in which the GPI anchor is replaced by one or more transmembrane domains, and in which the modified protein further includes a trafficking element that directs the so generated recombinant hybrid protein to a sub-cellular location favoring MHC-II presentation, and especially the recycling endosome, sorting endosome, or lysosome. Most typically, but not necessarily, the replacement of the GPI anchor can be effected by either removal of the GPI anchor signal sequence or by modification of the GPI anchor signal sequence (e.g., replacement of one or more amino acids) to abolish or render GPI modification less efficient. In less preferred aspects, however, GPI modification may also be done by adding a peptide linker to the C-terminus of the protein, followed by a transmembrane domain, or by adding a transmembrane domain to the C-terminus of the protein (here: without intervening linker).

With respect to contemplated transmembrane proteins, it should be recognized that many domains are deemed suitable herein, and that the modified protein may contain from one or more (e.g., two, three, four, six, etc.) transmembrane domains. For example, various receptor tyrosine kinases, cytokine receptors, receptor guanylyl cyclases, and receptor serine/threonine protein kinases contain a single transmembrane domain. In other examples, certain ion channels and adenylcyclases have six transmembrane domains, and selected cell surface receptors comprise seven transmembrane domains. Exemplary transmembrane proteins include the insulin receptor, the insulin-like growth factor receptor, the human growth hormone receptor, various glucose transporters, the transferrin receptor, the epidermal growth factor receptor, the LDL receptor, the leptin receptor, various interleukin receptors (e.g., IL-1 receptor, IL-2 receptor, etc.).

Most typically, contemplated transmembrane domains will include about 20 consecutive hydrophobic amino acids that may be followed by charged amino acids. There are numerous transmembrane domains known in the art, and all of them are deemed suitable for use herein. For example, contemplated transmembrane domains can comprise comprises the transmembrane region(s) of the alpha, beta, or zeta chain of the T-cell receptor, CD28, CD3 epsilon, CD45, CD4, CD5, CD8 (e.g., CD8 alpha, CD8 beta), CD9, CD16, CD22, CD33, CD37, CD64, CD80, CD86, CD134, CD137, CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2Ry, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, or PAG/Cbp.

Where multiple transmembrane domains are desired, it should be noted that the hybrid protein may have at least two, three, four, or five, or six transmembrane domains (or regions that include at least about 10 to 35 more preferably about 15 to 30 or 20 to 25 amino acid residues and have at least about 60%, 70%, 80%, 90%, 95%, 99%, or 100% homology with a known transmembrane domain. As will be readily appreciated, transmembrane domains can be identified by computational analysis of known amino acid sequences using prediction methods analyzing secondary structure, hydrophobicity, and/or topology of a protein in question (see e.g., *Biochemistry* (1994)33: 3038-3049). Moreover, where contemplated hybrid proteins have multiple transmembrane domains, individual transmembrane domains will typically be coupled to each other via intra-/extracellular loops, which may be formed from about 5-100 amino acids. Synthetic transmembrane domains may comprise repeat units of hydrophobic amino acids (e.g., F, W, V). Lastly, it should be appreciated that while use of a transmembrane domain is generally preferred, the transmembrane domain may also be omitted in at least some embodiments.

With respect to suitable trafficking elements, it is contemplated that preferred elements include a CD1b leader sequence, a CD1a tail, a CD1c tail, and a LAMP1-transmembrane sequence. For example, lysosomal targeting can be achieved using a LAMP1-TM (transmembrane) sequence, while recycling endosomes can be targeted via the CD1a tail targeting sequence, and sorting endosomes can be targeted via the CD1c tail targeting sequence as is shown in more detail further below.

In particular embodiments, the immunogenic peptides of the invention further comprise an amino acid sequence (or another organic compound) facilitating uptake of the peptide into (late) endosomes for processing and presentation within CD1d determinants. The late endosome targeting is mediated by signals present in the cytoplasmic tail of proteins and correspond to well-identified peptide motifs such as the dileucine-based motifs a tyrosine-based motif or the so-called acidic cluster motif. The symbol o represents amino acid residues with a bulky hydrophobic side chains such as Phe, Tyr and Trp. The late endosome targeting sequences allow for processing and efficient presentation of the antigen-derived T cell epitope by CD1d molecules. Such endosomal targeting sequences are contained, for example, within the gp75 protein (*J Cell Biol* 130, 807-820), the human CD3 gamma protein, the HLA-BMβ. (*J. Immunol.* (1996)157, 1017-1027), the cytoplasmic tail of the DEC205 receptor (J Cell Biol (2000)151, 673-683). Other examples of peptides which function as sorting signals to the endosome are disclosed in the review of Bonifacio and Traub (*Annu. Rev. Biochem.* (2003)72, 395-447. See also *Front Biosci* 2009.

Viewed from a different perspective, the hybrid proteins contemplated herein will include a trafficking signal that will result in preferential trafficking (e.g., at least 70%, more typically at least 80%, and most typically at least 90% of all expressed hybrid proteins are found in the targeted sub-cellular compartment) of the hybrid protein to the desired sub-cellular location. Therefore, in contemplated aspects of the inventive subject matter, signal and/or leader peptides may be used for trafficking neoepitopes and/or polytopes to the endosomal or lysosomal compartment. Thus, it should also be recognized that targeting presequences and/or targeting peptides can be employed. The presequences of the targeting peptide may be added to the N-terminus and/or C-terminus and typically comprise between 6-136 basic and hydrophobic amino acids. In case of peroxisomal targeting, the targeting sequence may be at the C-terminus. Other signals (e.g., signal patches) may be used and include sequence elements that are separate in the peptide sequence and become functional upon proper peptide folding.

In addition, protein modifications like glycosylations can induce targeting. Among other suitable targeting signals, the inventors contemplate peroxisome targeting signal 1 (PTS1), a C-terminal tripeptide, and peroxisome targeting signal 2 (PTS2), which is a nonapeptide located near the N-terminus. In addition, sorting of proteins to endosomes and lysosomes may also be mediated by signals within the cytosolic domains of the proteins, typically comprising short, linear sequences. Some signals are referred to as tyrosine-based sorting signals or as dileucine-based signals. All of these signals are recognized by components of protein coats peripherally associated with the cytosolic face of membranes. Other known signals are recognized with characteristic specificity by the adaptor protein (AP) complexes AP-1, AP-2, AP-3, and AP-4, whereas still other signals are recognized by another family of adaptors known as GGAs.

It should further be appreciated that the transmembrane domain(s) and the trafficking sequences may in some embodiments be coupled to the antigen via a linker, which is preferably a flexible linker comprises between 5 and 50 amino acids. For example, contemplated linkers include flexible glycine/serine linkers, and rigid linkers. There are various linker sequences known on the art (see e.g., Adv Drug Deliv Rev. 2013 Oct. 15; 65(10): 1357-1369), and all of these linkers are deemed suitable for use herein.

In still further contemplated embodiments, the recombinant hybrid protein may also be modified to facilitate trafficking to or retention in the cytosolic compartment (which may not necessarily require one or more specific sequence elements). For example, in at least some aspects, N- or C-terminal cytoplasmic retention signals may be added, including cytoplasmic retention signals of SNAP-25, syntaxin, synaptoprevin, synaptotagmin, vesicle associated membrane proteins (VAMPs), synaptic vesicle glycoproteins (SV2), high affinity choline transporters, neurexins, voltage-gated calcium channels, acetylcholinesterase, and NOTCH. Thus, it should be appreciated that peptides can be routed to specific cellular compartments to so achieve preferential or even specific presentation via MHC-I or MHC-II.

Still further contemplated increases in antigenicity of the recombinant hybrid proteins presented herein can be achieved by (mono/poly)ubiquitinylation via addition of one or more recombinant ubiquitination motifs. There are numerous motifs known in the art, and all of these are deemed suitable for use herein (see e.g., *Proteins* 2010 Feb. 1; 78(2): 365-380).

While not limiting to the inventive subject matter, the modified proteins will generally be expressed in vitro or in vivo from an appropriately constructed recombinant nucleic acid, and especially suitable recombinant nucleic acid include plasmids and viral nucleic acids. Where a viral nucleic acid is employed, it is particularly preferred that the nucleic acid is delivered via infection of the patient or patient cells by the virus. Therefore, contemplated compositions may be administered as a recombinant viral, yeast, or bacterial vaccine, or as a gemisch of multiple (typically distinct) proteins or hybrid polypeptides. Among other contemplated viral expression vectors and viruses, adenoviral vectors and viruses (e.g., E2b deleted AdV) are especially contemplated.

Viewed from a different perspective, it should be appreciated that the compositions and methods presented herein will deliver an otherwise poorly immunogenic antigen in a manner that facilitates MHC-II presentation. Indeed, such modified proteins can advantageously be tailored to achieve various specific immune reactions, including an enhanced CD4$^+$ immune response and surprisingly an enhanced CD8$^+$ immune response. In addition, contemplated hybrid proteins may be co-expressed or co-administered with other immune stimulatory compositions (that may preferably be encoded on the same recombinant nucleic acid). For example, a recombinant nucleic acid may be constructed that includes an expression cassette that encodes one or more of a co-stimulatory molecule, an immune stimulatory cytokine, and a protein that interferes with or down-regulates checkpoint inhibition. Suitable co-stimulatory molecules include OX40L, 4-1BBL, CD80, CD86, CD30, CD40, CD30L, CD40L, ICOS-L, B7-H3, B7-H4, CD70, GITR-L, TIM-3, TIM-4, CD48, CD58, TL1A, ICAM-1, and LFA3, and suitable immune stimulatory cytokines include IL-2, IL-12, IL-15, IL-15 super agonist (ALT803), IL-21, IPS1, and LMP1. In further contemplated aspects, preferred proteins that interfere with checkpoint inhibition include antibodies or antagonists of CTLA-4, PD-1, TIM1 receptor, 2B4, or CD160. Likewise, additionally encoded signals include protein adjuvants like calreticulin or HMBG proteins (or fragments thereof)

Therefore, in exemplary preferred aspects of the inventive subject matter, cancer immune therapy may uses a recombinant adenovirus that has as payload in which a modified TAA has a deleted or otherwise non-functional GPI anchor sequence and that also includes a transmembrane domain and a trafficking signal as described above. Regardless of the type of recombinant virus it is contemplated that the virus may be used to infect patient (or non-patient) cells ex vivo or in vivo. For example, the virus may be injected subcutaneously or intravenously, or may be administered intranasaly or via inhalation to so infect the patients cells, and especially antigen presenting cells. Alternatively, immune competent cells (e.g., NK cells, T cells, macrophages, dendritic cells, etc.) of the patient (or from an allogeneic source) may be infected in vitro and then transfused to the patient. Alternatively, immune therapy need not rely on a virus but may be effected with nucleic acid transfection or vaccination using RNA or DNA, or other recombinant vector that leads to the expression of the neoepitopes (e.g., as single peptides, tandem mini-gene, etc.) in desired cells, and especially immune competent cells.

Most typically, the desired nucleic acid sequences (for expression from virus infected cells) are under the control of appropriate regulatory elements well known in the art. For example, suitable promoter elements include constitutive strong promoters (e.g., SV40, CMV, UBC, EF1A, PGK, CAGG promoter), but inducible promoters are also deemed suitable for use herein, particularly where induction conditions are typical for a tumor microenvironment. For example, inducible promoters include those sensitive to hypoxia and promoters that are sensitive to TGF-β or IL-8 (e.g., via TRAF, JNK, Erk, or other responsive elements promoter). In other examples, suitable inducible promoters include the tetracycline-inducible promoter, the myxovirus resistance 1 (Mx1) promoter, etc. Alternatively, it should be appreciated that cancer vaccine compositions need not be limited to adenovirus constructs as described above, but may include recombinant yeast and bacteria as well as recombinant protein coupled to a carrier.

Where the expression construct is a viral expression construct (e.g., an adenovirus, and especially AdV with E1 and E2b deleted), it is contemplated that the recombinant viruses may then be individually or in combination used as a therapeutic vaccine in a pharmaceutical composition, typically formulated as a sterile injectable composition with a virus titer of between $10^6$-$10^{13}$ virus particles, and more typically between $10^9$-$10^{12}$ virus particles per dosage unit. Alternatively, virus may be employed to infect patient (or other HLA matched) cells ex vivo and the so infected cells are then transfused to the patient. In further examples, treatment of patients with the virus may be accompanied by allografted or autologous natural killer cells or T cells in a bare form or bearing chimeric antigen receptors expressing antibodies targeting neoepitope, neoepitopes, tumor associated antigens or the same payload as the virus. The natural killer cells, which include the patient-derived NK-92 cell line, may also express CD16 and can be coupled with an antibody.

Where desired, additional therapeutic modalities may be employed which may be neoepitope based (e.g., synthetic antibodies against neoepitopes as described in WO 2016/172722), alone or in combination with autologous or allogenic NK cells, and especially haNK cells or taNK cells (e.g., both commercially available from NantKwest, 9920 Jefferson Blvd. Culver City, CA 90232). Where haNK or taNK cells are employed, it is particularly preferred that the haNK cell carries a recombinant antibody on the CD16 variant that binds to a neoepitope of the treated patient, and where taNK cells are employed it is preferred that the chimeric antigen receptor of the taNK cell binds to a neoepitope of the treated patient. The additional treatment modality may also be independent of neoepitopes, and especially preferred modalities include cell-based therapeutics such as activated NK cells (e.g., aNK cells, commercially available from NantKwest, 9920 Jefferson Blvd. Culver City, CA 90232), and non cell-based therapeutics such as chemotherapy and/or radiation. In still further contemplated aspects, immune stimulatory cytokines, and especially IL-2, IL15, and IL-21 may be administered, alone or in combination with one or more checkpoint inhibitors (e.g., ipilimumab, nivolumab, etc.).

Similarly, it is still further contemplated that additional pharmaceutical intervention may include administration of one or more drugs that inhibit immune suppressive cells, and especially MDSCs Tregs, and M2 macrophages. Thus, suitable drugs include IL-8 or interferon-γ inhibitors or antibodies binding IL-8 or interferon-γ, as well as drugs that deactivate MDSCs (e.g., NO inhibitors, arginase inhibitors, ROS inhibitors), that block development of or differentiation of cells to MDSCs (e.g., IL-12, VEGF-inhibitors, bisphosphonates), or agents that are toxic to MDSCs (e.g., gemcitabine, cisplatin, 5-FU). Likewise, drugs like cyclophosphamide, daclizumab, and anti-GITR or anti-OX40 antibodies may be used to inhibit Tregs.

To trigger overexpression or transcription of stress signals, it is also contemplated that the chemotherapy and/or radiation for the patient may be done using a low-dose regimen, preferably in a metronomic fashion. For example, it is generally preferred that such treatment will use doses effective to affect at least one of protein expression, cell division, and cell cycle, preferably to induce apoptosis or at least to induce or increase the expression of stress-related genes (and particularly NKG2D ligands). Thus, in further contemplated aspects, such treatment will include low dose treatment using one or more chemotherapeutic agents. Most typically, low dose treatments will be at exposures that are equal or less than 70%, equal or less than 50%, equal or less than 40%, equal or less than 30%, equal or less than 20%, equal or less than 10%, or equal or less than 5% of the $LD_{50}$ or $IC_{50}$ for the chemotherapeutic agent. Additionally, where advantageous, such low-dose regimen may be performed in a metronomic manner as described, for example, in U.S. Pat. Nos. 7,758,891, 7,771,751, 7,780,984, 7,981,445, and 8,034,375.

With respect to the particular drug used in such low-dose regimen, it is contemplated that all chemotherapeutic agents are deemed suitable. Among other suitable drugs, kinase inhibitors, receptor agonists and antagonists, anti-metabolic, cytostatic and cytotoxic drugs are all contemplated herein. However, particularly preferred agents include those identified to interfere or inhibit a component of a pathway that drives growth or development of the tumor. Suitable drugs can be identified using pathway analysis on omics data as described in, for example, WO 2011/139345 and WO 2013/062505. Most notably, so achieved expression of stress-related genes in the tumor cells will result in surface presentation of NKG2D, NKP30, NKP44, and/or NKP46 ligands, which in turn activate NK cells to specifically destroy the tumor cells. Thus, it should be appreciated that low-dose chemotherapy may be employed as a trigger in tumor cells to express and display stress related proteins, which in turn will trigger NK-cell activation and/or NK-cell mediated tumor cell killing. Additionally, NK-cell mediated killing will be associated with release of intracellular tumor specific antigens, which is thought to further enhance the immune response.

EXAMPLES

Figure 2A:
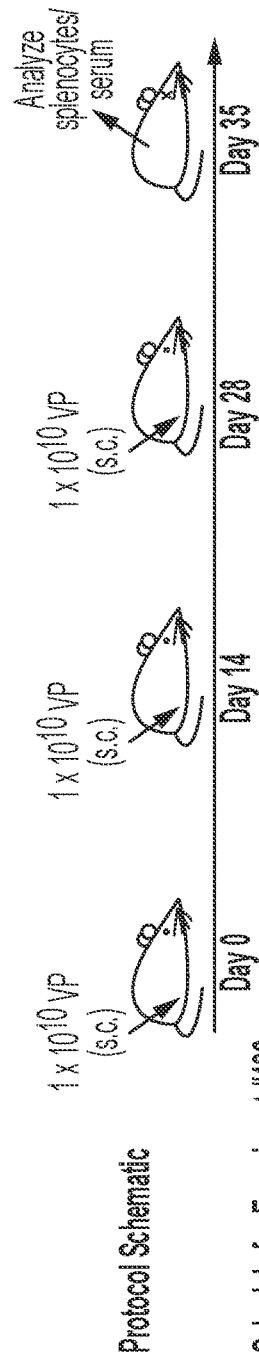
FIG. 2A is a schematic illustration of an exemplary immunization schedule/schematic according to the inventive subject matter.
Figure 2B:
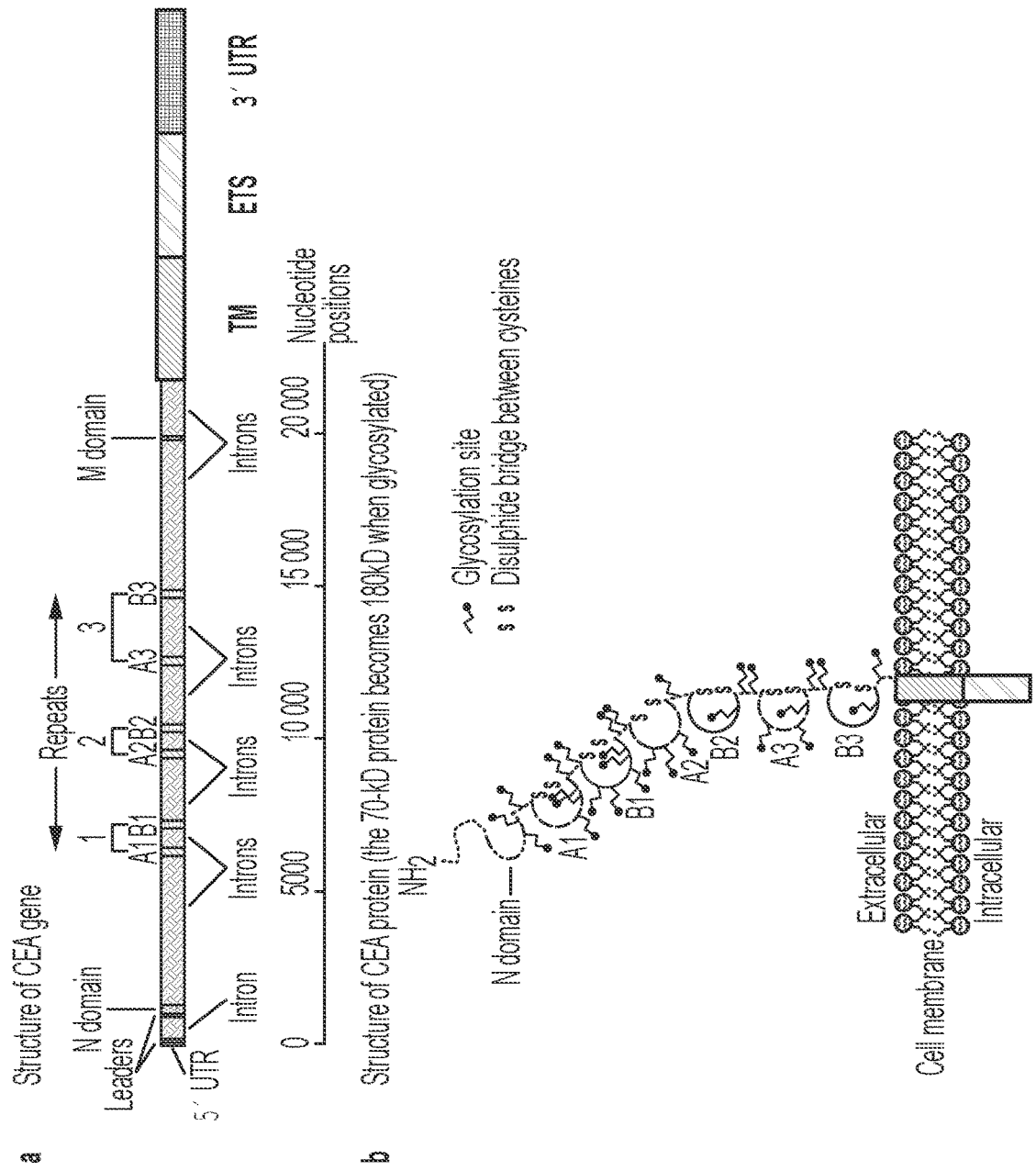
FIG. 2B is an exemplary schematic of recombinant constructs for modified CEA.

The inventor prepared various adenoviral expression constructs containing null payload (Group1), CEA payload (Group 2), CEA-CD1c payload (Group 3), CEA-LAMP1 payload (Group 4), CEA-CD1a payload (Group 5), and mice were immunized following a biweekly prime/boost regimen using $10^{10}$ viral particles per injection as shown FIG. 2A. All mice were euthanized at day 35 and splenocytes and peripheral blood were collected. FIG. 2B depicts schematically recombinant constructs used in the scheme of FIG. 2A.

Figure 3:
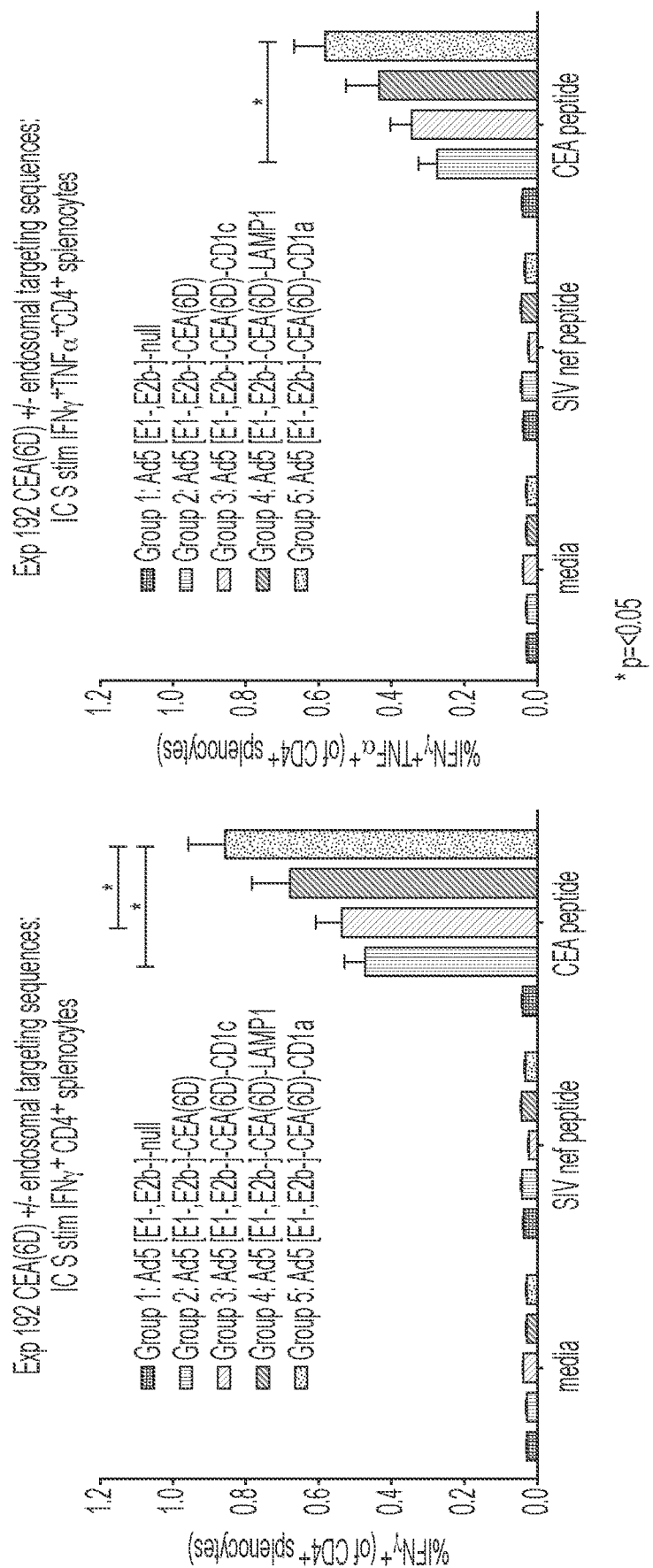
FIG. 3 shows exemplary results for CD4+ splenocytes following the immunization schedule of FIG. 2A.

FIG. 3 provides exemplary results with respect to CD4+ splenocytes. The left panel illustrates the fraction of ICS stim IFNγ+CD4+ cells that were observed in response to media (left), an unrelated peptide (SIV nef peptide, middle), and CEA peptide (right). As expected, no significant stimulation of CD4+ cells was found with media and unrelated protein. However, when exposed to CEA peptide, all CEA bearing adenoviral constructs resulted in a significant response, with a substantially enhanced response in those where trafficking was forced to the endo-/lysosomal compartments. Similarly, the fraction of IFNγ+ TNFα+ CD4+ cells was significantly increased with where trafficking was forced to the endo-/lysosomal compartments (right panel).

Figure 4:
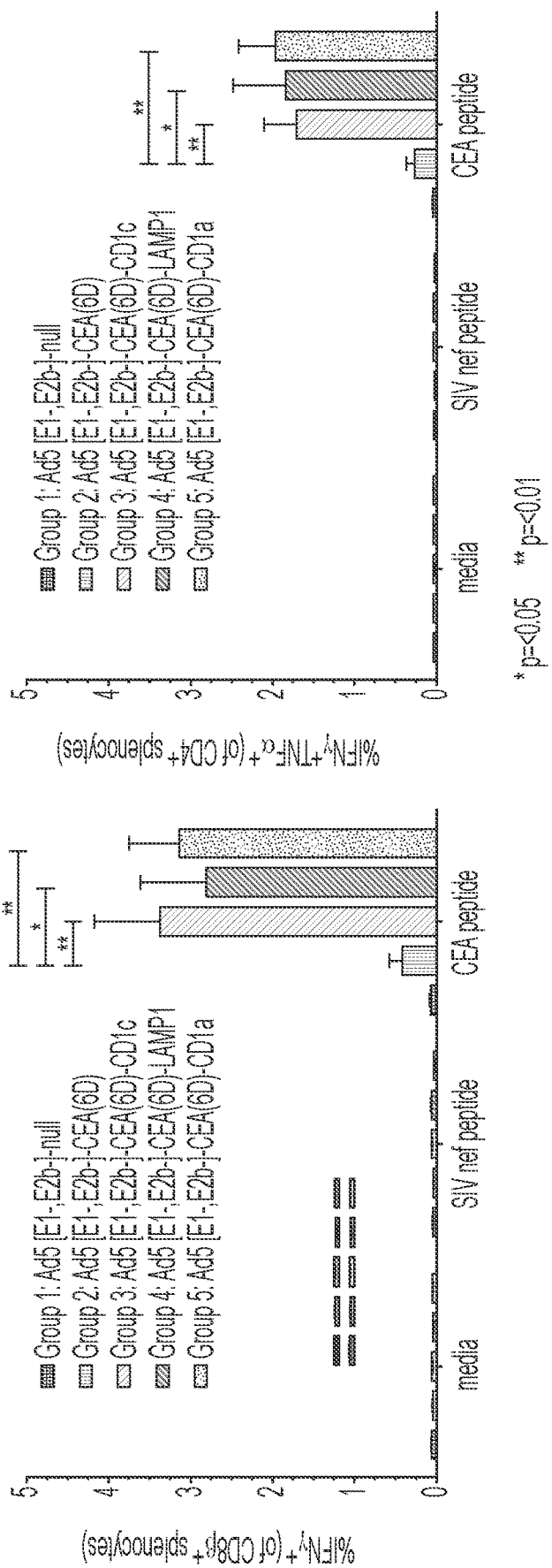
FIG. 4 shows exemplary results for CD8+ splenocytes following the immunization schedule of FIG. 2A.
Figure 5:
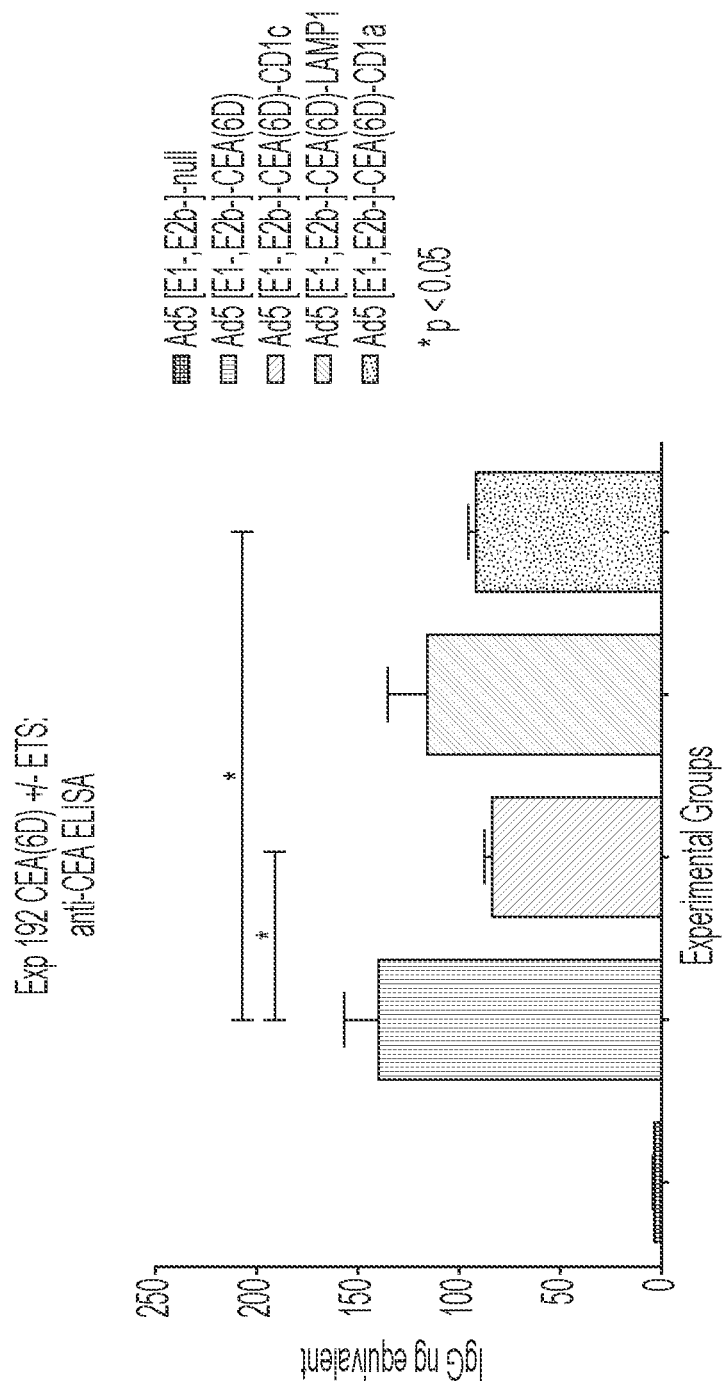
FIG. 5 shows exemplary ELISA results following the immunization schedule of FIG. 2A.

Even more notably, when the same experiments were used to observe CD8+ cells, the inventor discovered that IFNγ+ CD8+ as well as IFNγ+ TNFα+ CD8+ cells were significantly increased where trafficking was forced to the endo-/lysosomal compartments as can be taken from FIG. 4. Such enhancement was particularly pronounced vis-à-vis adenoviral delivery of CEA peptide alone. Indeed, the significant increase in reactive CD8+ cells is particularly unexpected in cases where the recombinant hybrid protein was targeted to the endosomal and/or lysosomal pathway (which is typically the route for MHC-I presentation). While not limiting to the inventive subject matter, it is contemplated that the recombinant hybrid proteins presented herein will advantageously be subject to a cross-presentation type antigen processing. Thus, it should be appreciated that contemplated systems and methods not only substantially enhance an immune response against an otherwise difficult to target antigen (GPI-anchored antigen), but also increase the fraction of polyfunctional CD4+ and CD8+ cells. Advantageously, all immunized animals were also able to produce significant quantities of antibodies as is shown in the graph depicting anti-CEA ELISA in FIG. 5.

The following sequences were used in the above experiments, with the leader peptide shown underlined, transmembrane domain shown in bold typeface, and endosomal targeting sequences shown in italics. All sequences were subcloned into and expressed from an E2b deleted adenovirus AdV that was injected subcutaneously into mice following the immunization schedule of FIG. 2A.

>CEA1 (SEQ ID NO: 1):
<u>MESPSAPPHRWCIPWQRLLLTASLLTFWNPPTT</u>AKLTIESTPFNVAEGKE

VLLLVHNLPQHLFGYSWYKGERVDGNRQIIGYVIGTQQATPGPAYSGREI

IYPNASLLIQNIIQNDTGFYTLHVIKSDLVNEEATGQFRVYPELPKPSIS

SNNSKPVEDKDAVAFTCEPETQDATYLWWVNNQSLPVSPRLQLSNGNRTL

TLFNVTRNDTASYKCETQNPVSARRSDSVILNVLYGPDAPTISPLNTSYR

SGENLNLSCHAASNPPAQYSWFVNGTFQQSTQELFIPNITVNNSGSYTCQ

AHNSDTGLNRTTVTTITVYAEPPKPFITSNNSNPVEDEDAVALTCEPEIQ

NTTYLWWVNNQSLPVSPRLQLSNDNRTLTLLSVTRNDVGPYECGIQNELS

VDHSDPVILNVLYGPDDPTISPSYTYYRPGVNLSLSCHAASNPPAQYSWL

IDGNIQQHTQELFISNITEKNSGLYTCQANNSASGHSRTTVKTITVSAEL

PKPSISSNNSKPVEDKDAVAFTCEPEAQNTTYLWWVNGQSLPVSPRLQLS

NGNRTLTLFNVTRNDARAYVCGIQNSVSANRSDPVTLDVLYGPDTPIISP

PDSSYLSGADLNLSCHSASNPSPQYSWRINGIPQQHTQVLFIAKITPNNN

GTYACFVSNLATGRNNSIVKSITVSASGTSPGLSAGATVGIMIGVLVGVA

LI

>CEA1-CD1a (SEQ ID NO: 2):
<u>MESPSAPPHRWCIPWQRLLLTASLLTFWNPPTT</u>AKLTIESTPFNVAEGKE

VLLLVHNLPQHLFGYSWYKGERVDGNRQIIGYVIGTQQATPGPAYSGREI

IYPNASLLIQNIIQNDTGFYTLHVIKSDLVNEEATGQFRVYPELPKPSIS

SNNSKPVEDKDAVAFTCEPETQDATYLWWVNNQSLPVSPRLQLSNGNRTL

TLFNVTRNDTASYKCETQNPVSARRSDSVILNVLYGPDAPTISPLNTSYR

SGENLNLSCHAASNPPAQYSWFVNGTFQQSTQELFIPNITVNNSGSYTCQ

AHNSDTGLNRTTVTTITVYAEPPKPFITSNNSNPVEDEDAVALTCEPEIQ

NTTYLWWVNNQSLPVSPRLQLSNDNRTLTLLSVTRNDVGPYECGIQNELS

VDHSDPVILNVLYGPDDPTISPSYTYYRPGVNLSLSCHAASNPPAQYSWL

IDGNIQQHTQELFISNITEKNSGLYTCQANNSASGHSRTTVKTITVSAEL

PKPSISSNNSKPVEDKDAVAFTCEPEAQNTTYLWWVNGQSLPVSPRLQLS

NGNRTLTLFNVTRNDARAYVCGIQNSVSANRSDPVTLDVLYGPDTPIISP

PDSSYLSGADLNLSCHSASNPSPQYSWRINGIPQQHTQVLFIAKITPNNN

GTYACFVSNLATGRNNSIVKSITVMLIPIAVGGALAGLVLIVLIAYLIGR

*KRCFC*

>CEA1-CD1c (SEQ ID NO: 3):
<u>MESPSAPPHRWCIPWQRLLLTASLLTFWNPPTT</u>AKLTIESTPFNVAEGKE

VLLLVHNLPQHLFGYSWYKGERVDGNRQIIGYVIGTQQATPGPAYSGREI

IYPNASLLIQNIIQNDTGFYTLHVIKSDLVNEEATGQFRVYPELPKPSIS

SNNSKPVEDKDAVAFTCEPETQDATYLWWVNNQSLPVSPRLQLSNGNRTL

TLFNVTRNDTASYKCETQNPVSARRSDSVILNVLYGPDAPTISPLNTSYR

SGENLNLSCHAASNPPAQYSWFVNGTFQQSTQELFIPNITVNNSGSYTCQ

AHNSDTGLNRTTVTTITVYAEPPKPFITSNNSNPVEDEDAVALTCEPEIQ

NTTYLWWVNNQSLPVSPRLQLSNDNRTLTLLSVTRNDVGPYECGIQNELS

VDHSDPVILNVLYGPDDPTISPSYTYYRPGVNLSLSCHAASNPPAQYSWL

IDGNIQQHTQELFISNITEKNSGLYTCQANNSASGHSRTTVKTITVSAEL

PKPSISSNNSKPVEDKDAVAFTCEPEAQNTTYLWWVNGQSLPVSPRLQLS

NGNRTLTLFNVTRNDARAYVCGIQNSVSANRSDPVTLDVLYGPDTPIISP

PDSSYLSGADLNLSCHSASNPSPQYSWRINGIPQQHTQVLFIAKITPNNN

GTYACFVSNLATGRNNSIVKSITVMLIPIAVGGALAGLVLIVLIAYLIG

*KKHCSYQDIL*

>CEA1-LAMP1 (SEQ ID NO: 4):
<u>MESPSAPPHRWCIPWQRLLLTASLLTFWNPPTT</u>AKLTIESTPFNVAEGKE

VLLLVHNLPQHLFGYSWYKGERVDGNRQIIGYVIGTQQATPGPAYSGREI

IYPNASLLIQNIIQNDTGFYTLHVIKSDLVNEEATGQFRVYPELPKPSIS

SNNSKPVEDKDAVAFTCEPETQDATYLWWVNNQSLPVSPRLQLSNGNRTL

TLFNVTRNDTASYKCETQNPVSARRSDSVILNVLYGPDAPTISPLNTSYR

SGENLNLSCHAASNPPAQYSWFVNGTFQQSTQELFIPNITVNNSGSYTCQ

AHNSDTGLNRTTVTTITVYAEPPKPFITSNNSNPVEDEDAVALTCEPEIQ

NTTYLWWVNNQSLPVSPRLQLSNDNRTLTLLSVTRNDVGPYECGIQNELS

VDHSDPVILNVLYGPDDPTISPSYTYYRPGVNLSLSCHAASNPPAQYSWL

IDGNIQQHTQELFISNITEKNSGLYTCQANNSASGHSRTTVKTITVSAEL

PKPSISSNNSKPVEDKDAVAFTCEPEAQNTTYLWWVNGQSLPVSPRLQLS

NGNRTLTLFNVTRNDARAYVCGIQNSVSANRSDPVTLDVLYGPDTPIISP

PDSSYLSGADLNLSCHSASNPSPQYSWRINGIPQQHTQVLFIAKITPNNN

GTYACFVSNLATGRNNSIVKSITVMLIPIAVGGALAGLVLIVLIAYLIGR

*KRSHAGYQTI*

As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.). Most preferably, the recombinant virus is administered via subcutaneous or subdermal injection. However, in other contemplated aspects, administration may also be intravenous injection. Alternatively, or additionally, antigen presenting cells may be isolated or grown from cells of the patient, infected in vitro, and then transfused to the patient. Therefore, it should be appreciated that contemplated systems and methods can be considered a complete drug discovery system (e.g., drug discovery, treatment protocol, validation, etc.) for highly personalized cancer treatment.

The recitation of ranges of values herein is merely intended to serve as a shorthand method of referring individually to each separate value falling within the range.

Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A recombinant nucleic acid, comprising:
a sequence segment encoding a hybrid protein, wherein the hybrid protein comprises an antigen coupled to at least one transmembrane domain and a trafficking element;
wherein the antigen is a glycophosphatidylinositol (GPI)-anchored protein CEA (carcinoembryonic antigen), and wherein the GPI anchor signal sequence is removed or modified to abolish or render GPI binding less efficient;
wherein the transmembrane domain is defined by SEQ ID NO:5;
wherein the trafficking element is CD1a (Cluster of Differentiation 1a), CD1c (Cluster of Differentiation 1c), or Lamp1 (Lysosome-associated membrane glycoprotein 1), and directs the recombinant hybrid protein to a sub-cellular location selected from the group consisting of a recycling endosome, a sorting endosome, and a lysosome; and
wherein the sequence segment is operably linked to a promoter to drive expression of the hybrid protein.

2. The recombinant nucleic acid of claim 1, wherein the nucleic acid is a viral expression vector or wherein the viral expression vector is an adenoviral expression vector, optionally having a deleted E1 (early region 1) and E2b (early region 2b) gene.

3. The recombinant nucleic acid of claim 1, wherein the promoter is a constitutive promoter or an inducible promoter.

4. The recombinant nucleic acid of claim 1, wherein the recombinant nucleic acid further comprises a sequence that encodes at least one of a co-stimulatory molecule, an immune stimulatory cytokine, a protein that interferes with or down-regulates checkpoint inhibition, and an adjuvant polypeptide.

5. The recombinant nucleic acid of claim 4, wherein the adjuvant polypeptide is calreticulin or HMGB1 (High mobility group box 1).

6. The recombinant nucleic acid of claim 1, wherein the transmembrane domain is bound to the C-terminus of the antigen, or wherein the transmembrane domain is coupled to the C-terminus of the antigen via a peptide linker.

7. The recombinant nucleic acid protein of claim 1, wherein the trafficking element is bound in-frame to the C-terminus of the transmembrane domain.

8. The recombinant nucleic acid of claim 1, wherein the hybrid protein comprises the polypeptide sequence of SEQ ID NO:2.

9. The recombinant nucleic acid of claim 1, wherein the hybrid protein comprises the polypeptide sequence of SEQ ID NO:3.

10. The recombinant nucleic acid of claim 1, wherein the hybrid protein comprises the polypeptide sequence of SEQ ID NO:4.

11. A recombinant virus comprising the recombinant nucleic acid of claim 1.

12. The recombinant virus of claim 11, wherein the recombinant virus is a replication deficient virus.

13. A recombinant antigen presenting cell comprising the recombinant nucleic acid of claim 1.

14. The recombinant nucleic acid of claim 3, wherein the inducible promoter is inducible by hypoxia, IFN-gamma, or IL-8.

15. The recombinant nucleic acid of claim 4, wherein the wherein the co-stimulatory molecule is selected from the group consisting of OX40L, 4-1BBL, CD (Cluster of Differentiation)-80, CD86, CD30, CD40, CD30L, CD40L, ICOS-L, B7-H3, B7-H4, CD70, GITR-L, TIM-3, TIM-4, CD48, CD58, TLIA, ICAM-1, and LFA3.

16. The recombinant nucleic acid of claim 4, wherein the immune stimulatory cytokine is selected from the group consisting of IL-2 (Interleukin-2), IL-12 (Interleukin-12), IL-15 (Interleukin-15), IL-15 super agonist (ALT803), IL-21 (Interleukin-21), IPS1 (IFN-β promoter stimulator 1), and LMP1 (Latent membrane protein 1).

17. The recombinant nucleic acid of claim 4, wherein the protein that interferes with or down-regulates checkpoint inhibition is an antibody; or an antagonist selected from the group consisting of CTLA-4 (Cytotoxic T-lymphocyte associated protein 4), PD-1 (Programmed cell death protein 1), TIM1 (T-cell immunoglobulin and mucin domain 1) receptor, 2B4, and CD160.

18. The recombinant virus of claim 11, wherein the recombinant virus is an adenovirus having a deleted E1 and E2b gene.

* * * * *